(12) United States Patent
Eversmann et al.

(10) Patent No.: US 7,470,352 B2
(45) Date of Patent: Dec. 30, 2008

(54) SENSOR ARRANGEMENT

(75) Inventors: Bjorn-Oliver Eversmann, Munich (DE); Christian Paulus, Weilheim (DE); Guido Stromberg, Munich (DE); Roland Thewes, Grobenzell (DE)

(73) Assignee: Infineon Technologies AG, Neubiberg (DE)

( * ) Notice: Subject to any disclaimer, the term of this patent is extended or adjusted under 35 U.S.C. 154(b) by 944 days.

(21) Appl. No.: 10/826,881

(22) Filed: Apr. 16, 2004

(65) Prior Publication Data

US 2005/0029099 A1    Feb. 10, 2005

Related U.S. Application Data

(63) Continuation of application No. PCT/DE02/03098, filed on Aug. 23, 2002.

(30) Foreign Application Priority Data

Oct. 16, 2001 (DE) ................................. 101 51 021

(51) Int. Cl.
*G01N 27/403* (2006.01)
*G01N 27/327* (2006.01)
*G01N 27/414* (2006.01)
*G01D 18/00* (2006.01)
*C12Q 1/68* (2006.01)
*G11C 11/36* (2006.01)

(52) U.S. Cl. .................. 204/412; 204/411; 204/403.01; 204/403.03; 257/253; 378/207; 435/6; 365/175

(58) Field of Classification Search .................. 378/207; 435/6; 365/175; 204/411, 412; 257/253
See application file for complete search history.

(56) References Cited

U.S. PATENT DOCUMENTS

| 3,668,543 | A | * | 6/1972 | Bailey ......................... 330/260 |
| 5,250,168 | A | * | 10/1993 | Tsukada et al. ............. 204/416 |
| 5,902,044 | A | | 5/1999 | Pricer et al. |
| 5,965,452 | A | | 10/1999 | Kovacs |
| 6,031,606 | A | * | 2/2000 | Bayer et al. ............... 356/141.5 |
| 6,154,580 | A | | 11/2000 | Kuriyama et al. |
| 6,512,543 | B1 | * | 1/2003 | Kuroda et al. ............... 348/302 |
| 6,593,588 | B1 | * | 7/2003 | Reimer ....................... 250/573 |

(Continued)

FOREIGN PATENT DOCUMENTS

WO    WO-99/33018 A1    7/1999

(Continued)

*Primary Examiner*—Alex Noguerola
(74) *Attorney, Agent, or Firm*—Dickstein, Shapiro, LLP.

(57) ABSTRACT

Sensor arrangement having row and column lines arranged in first and second directions, respectively, sensor arrays arranged in crossover regions of the row and column lines, a detector, and a decoding device. The sensor arrays have a coupling device for electrically coupling respective row and column lines, and a sensor element to influence electric current flow through the coupling device. The detector is electrically coupled to a respective end section of at least a portion of the row and column lines, and detects a respective accumulative current flow from the individual electrical current flows provided by the sensor arrays of the respective lines. The decoding device is coupled to the row and column lines, and evaluates at least a portion of the accumulative electric current flows fed to the decoding device via the row and column lines to determine at which of the sensor elements a sensor signal is present.

27 Claims, 8 Drawing Sheets

U.S. PATENT DOCUMENTS

| | | | |
|---|---|---|---|
| 6,646,912 B2 * | 11/2003 | Hurst et al. | 365/175 |
| 6,667,632 B2 * | 12/2003 | Murakawa et al. | 324/770 |
| 2002/0039743 A1 * | 4/2002 | Hashimoto et al. | 435/6 |
| 2003/0058998 A1 * | 3/2003 | Aufrichtig et al. | 378/207 |

FOREIGN PATENT DOCUMENTS

| | | |
|---|---|---|
| WO | WO-00/62048 A2 | 10/2000 |

* cited by examiner

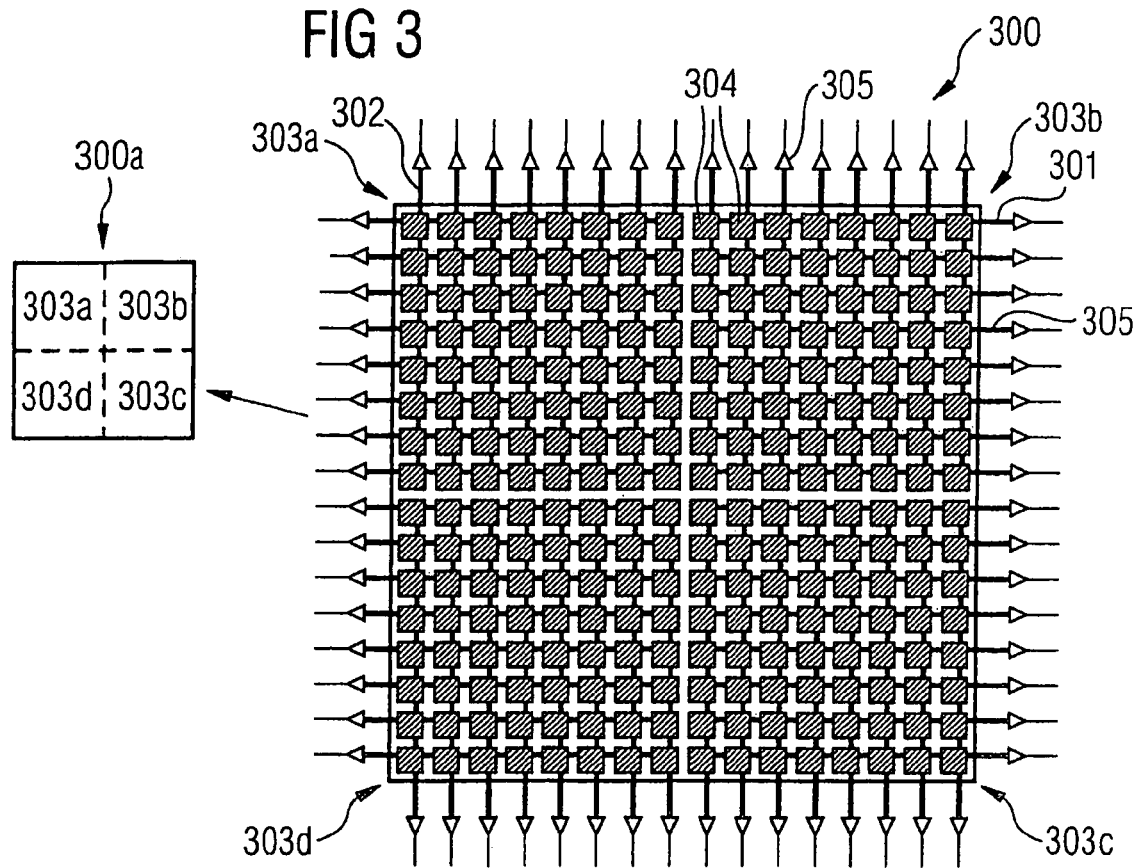
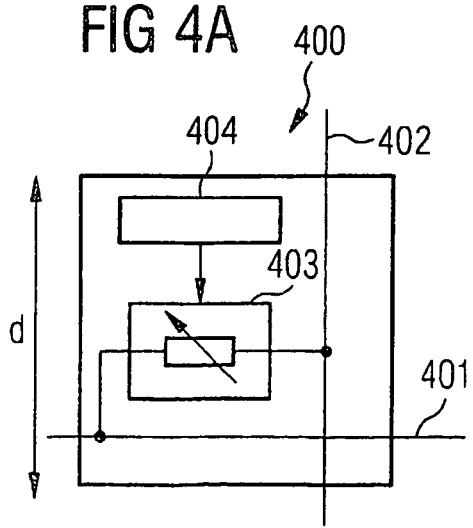
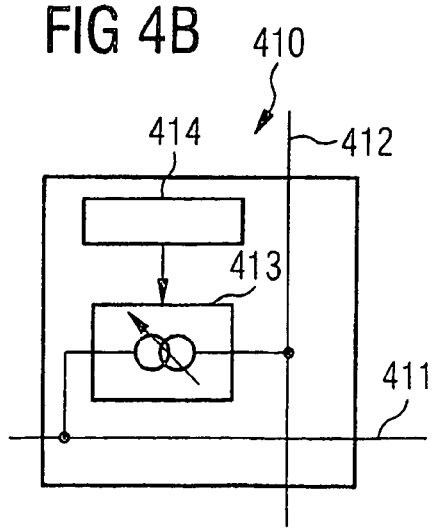

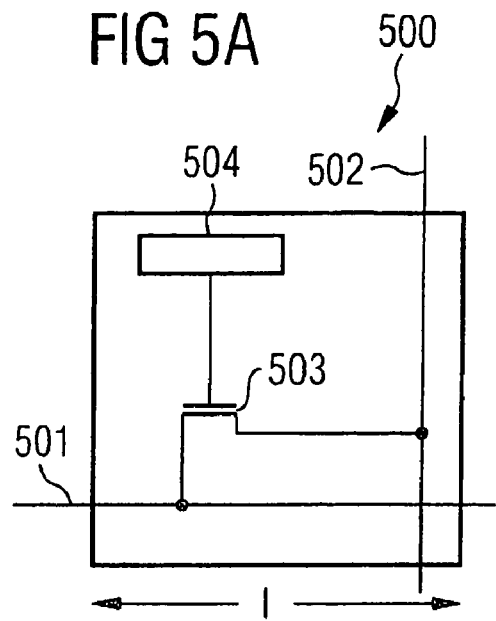
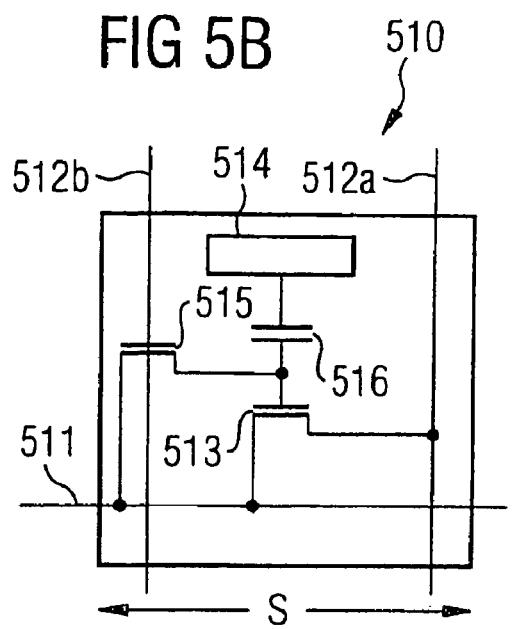
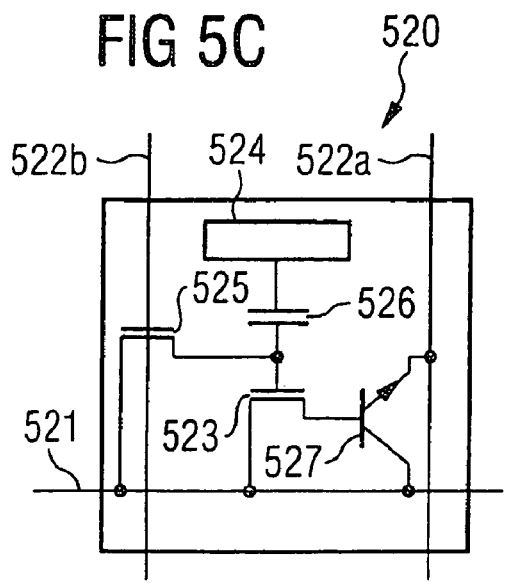
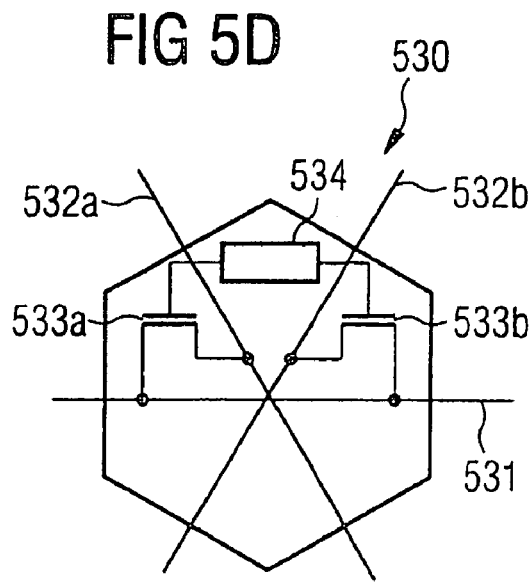

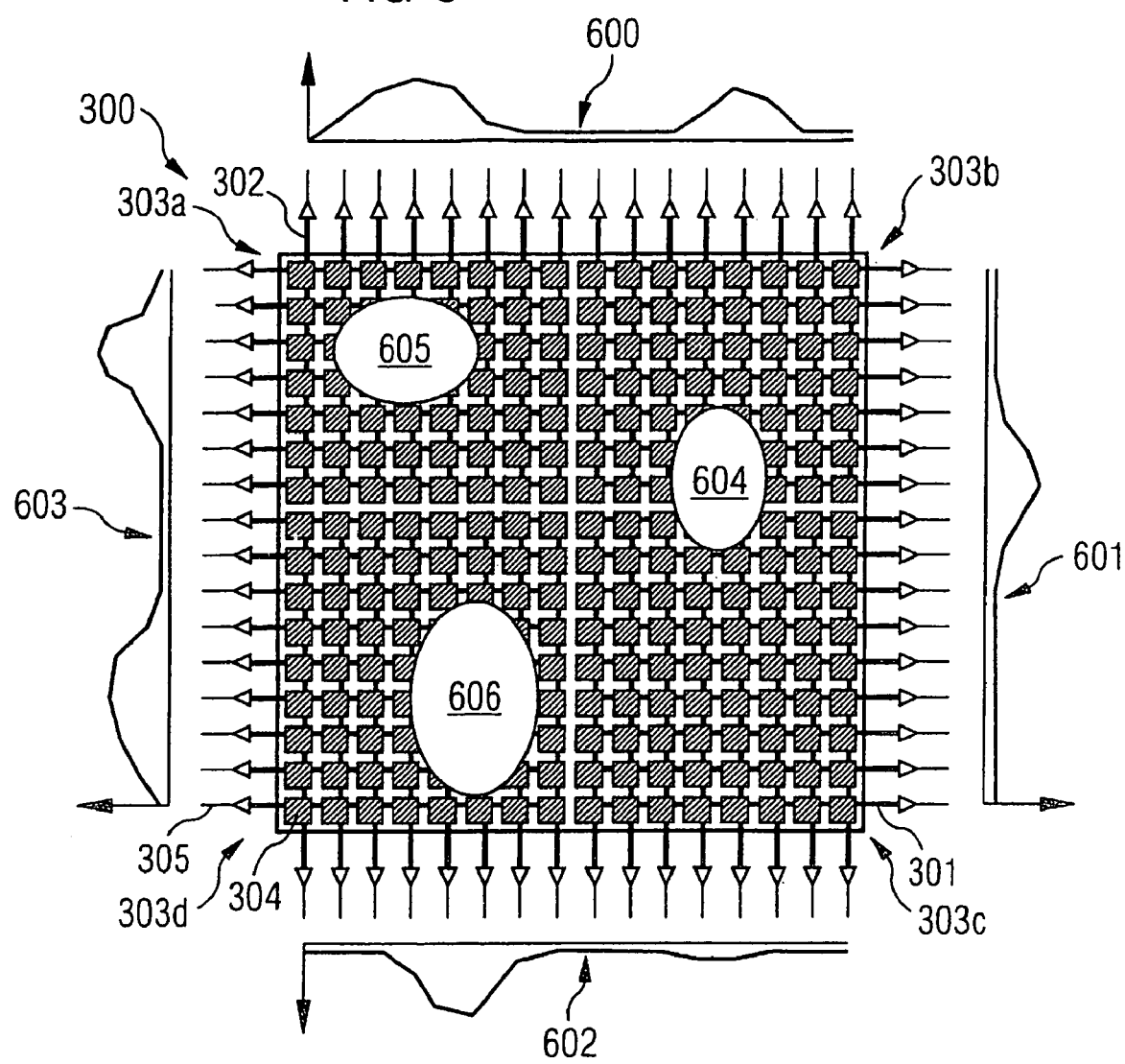

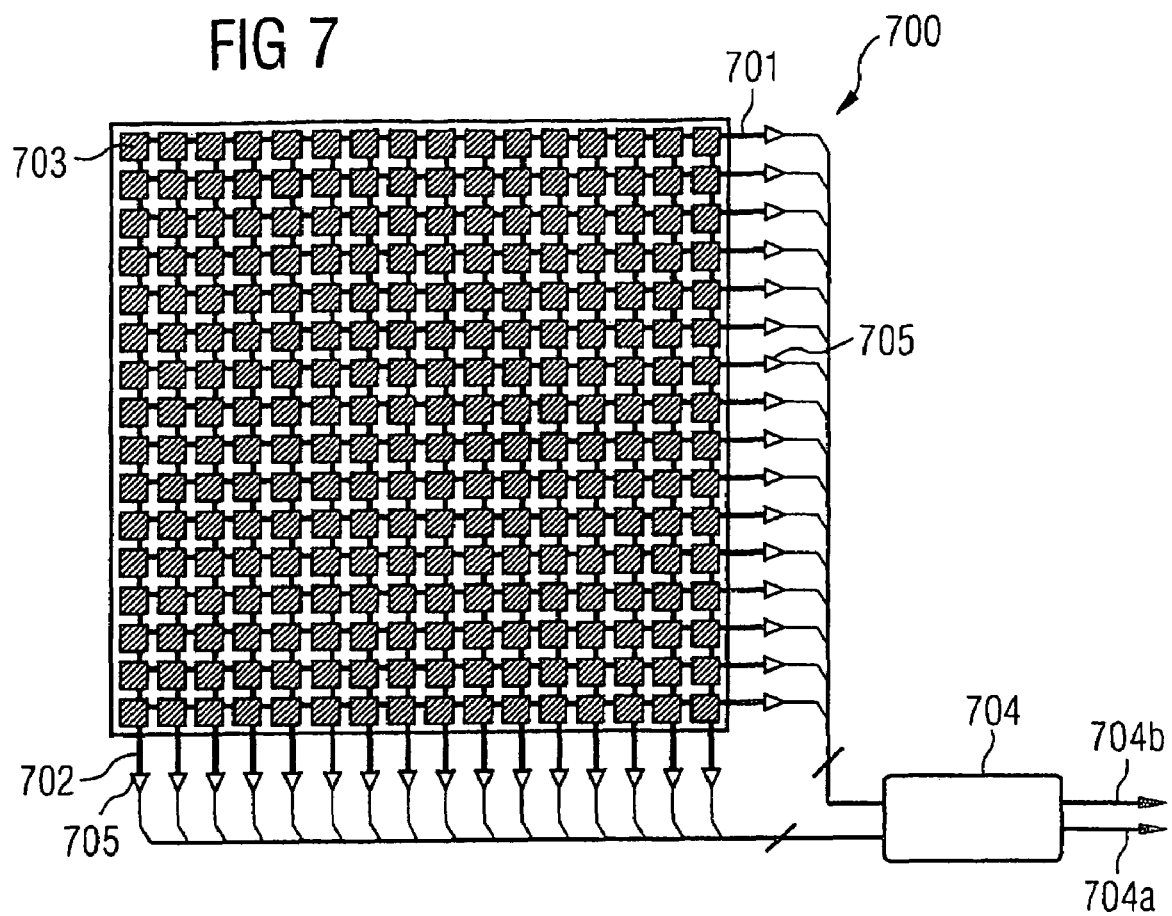
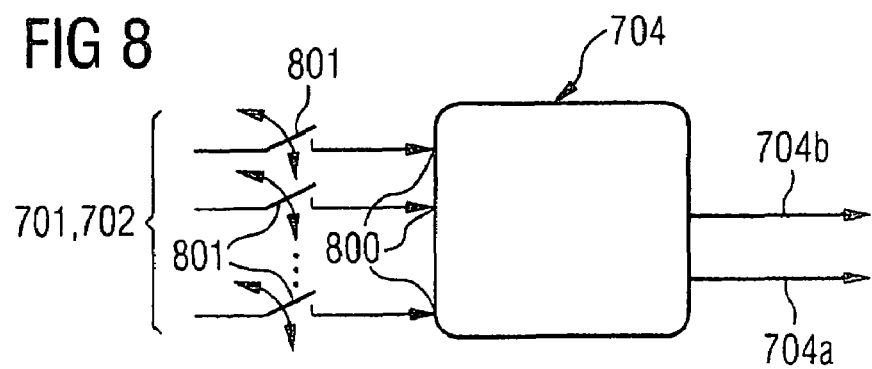

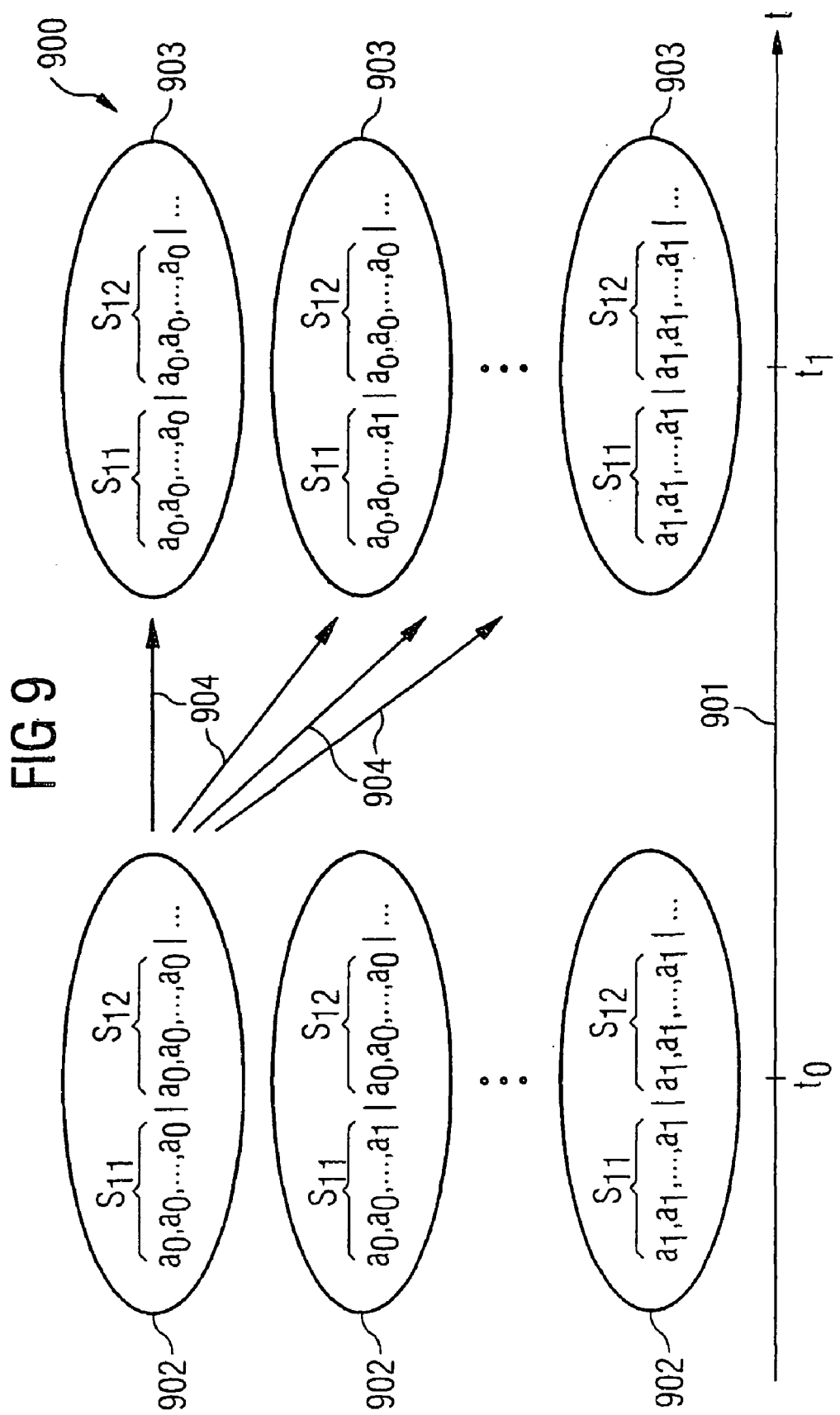

SENSOR ARRANGEMENT

CROSS-REFERENCE TO RELATED APPLICATION

This application is a continuation of International Patent Application Serial No. PCT/DE02/03098, filed Aug. 23, 2002, which published in German on May 8, 2003 as WO 03/038423 A2, and is incorporated herein by reference in its entirety.

FIELD OF THE INVENTION

The invention relates to a sensor arrangement.

BACKGROUND OF THE INVENTION

Present-day developments in many fields of science and technology are characterized by the fact that areas formerly independent of one another are increasingly being combined. One example of an interdisciplinary area is the interface between biology and semiconductor technology. A topic of present-day research is, by way of example, the economically very interesting coupling between biological cell assemblages (such as neurons, for example) and silicon microelectronics.

In accordance with one concept, a biological system is grown on the surface of a semiconductor-technological sensor and is examined in spatially or temporally resolved fashion by means of sensor electrodes arranged in matrix form on the surface of the sensor. In accordance with this concept, the metabolism parameters of the cells can be recorded for example by detecting local pH values with the aid of ion-sensitive field-effect transistors (ISFETs). In terms of its basic principle, an ISFET is constructed similarly to a metal-insulator-semiconductor field-effect transistor (MISFET). It differs from conventional MISFETs in that the conductivity of the channel region is not controlled by means of a metal electrode, but rather by means of an arrangement having an ion-sensitive layer, an electrolyte and a reference electrode. In other words, electrically charged biological molecules control the conductivity of the ISFET, which is detected as a sensor variable.

Examining the reaction of a biological system to an electrical stimulation is of particular interest. Neurons (nerve cells) can generate a small electric current via ion channels in the cell membranes in specific regions of their surface, said current being detected by a sensor situated underneath. Such pulses typically last a few milliseconds, and the electrical voltage that forms as a result is often less than 1 mV. In order to achieve a sufficient spatial resolution, the distance between neighboring sensor electrodes in the horizontal and vertical direction on a sensor surface that is often arranged in matrix form should preferably be less than 20 µm, so that the surface of a sensor and the cross-sectional area of a cell are approximately of the same order of magnitude. These requirements can be achieved by means of silicon microtechnology.

In the case of sensor arrangements having a sufficiently small number of sensor arrays, in accordance with the prior art, the output signal of each sensor array is passed out of the matrix by means of a dedicated line and processed further. In the case of a larger number of sensor arrays or decreasing distances between neighboring sensor arrays, this principle encounters its limits owing to the high space requirement of the high number of lines.

Referring to FIGS. 1A and 1B, a description is given below of a concept which is known from the prior art and makes it possible to read larger or increasingly dense arrangements of sensor electrodes. FIG. 1A shows a sensor arrangement 100 having a multiplicity of sensor electrodes 101 arranged in matrix form. The sensor electrodes 101 are (at least partly) coupled to one another by means of row lines 102 and column lines 103. An electrical amplifier device 104 is in each case arranged in edge regions of the row lines 102. As is furthermore shown in FIG. 1A, the matrix-type sensor arrangement 100 is divided into a first matrix region 105 and a second matrix region 106, which can be operated independently of one another. In a manner similar to that during the operation of a memory arrangement, the output signal of a specific sensor electrode 101 is switched onto a common output line of a row or column via switch elements 111 (cf., FIG. 1B) within the sensor arrangement 100. In accordance with the concept shown in FIGS. 1A and 1B, the quantity of data that is to be read out and to be processed constitutes the limits of the performance of the system. If a sensor arrangement is intended to be operated with a sufficiently high spatial resolution (i.e., sufficiently many sensor electrodes arranged sufficiently densely) and with a sufficiently high temporal resolution (i.e., a sufficiently high read-out frequency) and also with a sufficiently high accuracy, then the quantity of data to be read out per time rises to values which can make requirements of the technologically available equipment that cannot be achieved at the present time. The signals on the row lines 102 and the column lines 103 cannot be passed out of the sensor arrangement 100 in parallel owing to the still very large number of lines. The requirements made of the high quantity of data of the nm sensor electrodes to be read in the case of a matrix having m rows and n columns can exceed the performance of known technologies.

FIG. 1B illustrates a sensor electrode 101 in detail. The sensor electrode 101 is coupled to one of the row lines 102 and to one of the column lines 103. If a switch element 111 is closed, then the assigned sensor electrode 101 is selected and can be read. The sensor event detected by the sensor area 112 in the form of an electrical signal is amplified by means of an amplifier element 110 before it is communicated via the row line 102 to the edge of the sensor arrangement 100 illustrated in FIG. 1A.

To summarize, sensor arrangements for the spatially resolved and temporally resolved detection of analog electrical signals which are known from the prior art have the disadvantage, in particular, that the nm sensor electrodes have to be read individually and the signals have to be forwarded to a signal-processing circuit portion. As a result, in the case of a high number nm of sensor electrodes (m rows, n columns), large quantities of data that are to be processed rapidly occur, and have to be passed out of the matrix in amplified fashion with sufficient accuracy. This exceeds the performance limit of known concepts given the increasing requirements made of the spatial and temporal resolution of such systems.

WO 00/62048 A2 discloses an electrically driveable sensor arrangement having a multiplicity of arrays, suitable for the electrochemical detection of molecular substances and suitable for transporting or for handling charged molecules.

SUMMARY OF THE INVENTION

The invention is based on the problem of providing a sensor arrangement with an increased spatial and temporal resolution.

The problem is solved by means of a sensor arrangement having the features in accordance with the independent patent claim.

The sensor arrangement according to the invention has a plurality of row lines arranged in a first direction, a plurality of column lines arranged in at least one second direction, and a plurality of sensor arrays arranged in crossover regions of row lines and column lines. Each sensor array has at least one coupling device for electrically coupling a respective row line to a respective column line, and a sensor element assigned to the at least one coupling device, the sensor element being set up in such a way that the sensor element influences the electric current flow through the at least one assigned coupling device. Furthermore, the sensor arrangement of the invention has a means which is electrically coupled to a respective end section of at least a portion of the row lines and of at least a portion of the column lines and serves for detecting a respective accumulative current flow from the individual electrical current flows provided by the sensor arrays of the respective lines. Furthermore, the sensor arrangement has a decoding device, which is coupled to the row lines and the column lines and is set up in such a way that those sensor elements at which a sensor signal is present can be determined from at least a portion of the accumulative electric current flows which can be fed to the decoding device via the rows lines and the column lines.

It should be emphasized that the nomenclature "row line" and "column line" does not employ an orthogonal matrix. The row lines running in a first direction and the column lines running in at least one second direction may form any desired angles with one another. According to the invention, it is possible for as many different lines as desired to be laid at any desired angles over the sensor arrangement and for coupling devices to be interconnected in crossover regions, which coupling devices "branch off" a specific electric current from one line into the other line. One of the at least one second direction may, but need not, run orthogonally with respect to the first direction. The rows lines arranged along the first direction are provided, in particular, preferably for current feeding (but also for current discharging), and the column lines arranged along the at least one second direction are provided, in particular, preferably for current discharging.

A basic idea of the invention is based, differently than in accordance with the prior art, on not individually reading each of the nm matrix elements of a matrix having m rows and n columns, but rather on reading out in each case the accumulative signals along a row and along a column and combining the row and column signals with one another, or evaluating them computationally, by means of a correlation calculation in a decoding device in such a way that the sensor signals of the individual sensor elements can be deduced. What is thereby achieved is that, instead of nm signals of each sensor array, only n+m signals of the rows and columns have to be read out. Particularly in the case of high values of n and m, considerable numerical advantages are associated with this and higher read-out rates can consequently can be achieved. Conversely, given a fixed read-out rate, it is possible to reduce the dimensions of the individual sensor arrays and therefore to achieve an improved spatial resolution.

The invention exploits the fact that often only a small number of sensor elements of the sensor arrangement supply a signal. By way of example, in the case of an application relating to the examination of neurons grown on the surface of a sensor arrangement, it is often the case that only nutrient solution or tissue which is such that it does not supply an electrical signal is situated on most of the sensor elements of a sensor arrangement. In that case, with an active sensor element, the corresponding row line and the corresponding column line have a correlated signal, it being possible to determine, on the basis of the correlation, that sensor element on which the sensor event took place. By way of example, if the sensor element arranged in the k-th row and the l-th column of the sensor arrangement detects a sensor event, then an individual current flow is fed essentially simultaneously into the k-th row line and into the l-th column line. Upon the occurrence of temporally correlated or intensity-correlated current flows in the k-th row line and the l-th column line, it is possible to deduce that sensor element at which the sensor event took place.

Whereas in known realizations of sensor arrangements, all the sensor arrays are read successively and, therefore, nm signals are determnined in one cycle, only n+m signals are output and digitized in the realization according to the invention. Consequently, it is possible to achieve significantly increased sampling rates, i.e., a significantly improved temporal resolution of the sensor arrangement.

A further advantage is that a genuine snapshot of the potential conditions on the active sensor surface is possible. Whereas in the conventional case the matrix elements are read successively and are thus detected in a manner temporally staggered with respect to one another, the instantaneous situation can be "retained" and subsequently evaluated in the case of the invention. This results inter alia from the small number of electrical signals to be read out, which can be read out virtually instantaneously.

Furthermore the sensor arrangement according to the invention has the advantage that switching functions for the selection of a sensor array are unnecessary within the sensor arrangement. This is necessary in accordance with the prior art for the selection of a specific sensor array and results in a high susceptibility to interference on account of instances of capacitive coupling in from one switched line to other lines, for example measurement lines. The invention thereby increases the detection sensitivity. The invention likewise suppresses undesirable interactions between a sensor array and the examination object arranged thereon (for example a neuron) on account of instances of galvanic, inductive or capacitive coupling in.

Preferred developments emerge from the dependent claims.

In particular, the decoding device of the sensor arrangement according to the invention may be divided into a row decoding device, to which the accumulative electric current flows of the row lines can be fed, and a column decoding device, to which the accumulative electric current flows of the column lines can be fed, the row decoding device being set up in such a way that information about those sensor elements at which a sensor signal is possibly present can be determined from at least a portion of the accumulative electric current flows of the row lines independently of the accumulative current flows of the column lines; the column decoding device being set up in such a way that information about those sensor elements at which a sensor signal is possibly present can be determined from at least a portion of the accumulative electric current flows of the column lines independently of the accumulative current flows of the row lines; the decoding device being set up in such a way that those sensor elements at which a sensor signal is present can be determined by means of joint evaluation of the information determined by the row decoding device and the column decoding device.

By virtue of the fact that, illustratively, the accumulative current flows of the row lines and of the column lines are first of all decoded independently of one another, the decoding speed is increased and possible with a lower outlay on resources. By finding simultaneous activation patterns of the sensor arrays in row and column lines, it is possible to determine the position of the active sensors by adjusting the accumulative current flows in the row and column lines. It is also possible for even the accumulative current flows of different row lines (or different column lines) first of all to be evaluated independently of the accumulative current flows of other row lines (or other column lines) and for these separate results then to be adjusted.

Furthermore, the decoding device may be set up in such a way that those sensor elements at which a sensor signal is present are determined by carrying out a Fourier transformation of the time-dependent accumulative current flows of the row lines and of the column lines; multiplying together in pairs the Fourier-transformed accumulative current flows of the row lines and of the column lines; carrying out an inverse Fourier transformation with the accumulative current flows multiplied together in pairs.

In other words, during the correlation calculation, the time-dependent accumulative current flows of all the row and column lines are subjected to a Fourier transformation (from the time domain to the frequency domain) and are multiplied together in pairs in the frequency domain. An inverse Fourier transformation of this product of the accumulative current flows in row and column lines from the frequency domain to the time domain then supplies the original signal in the time domain at those sensor arrays located at the crossover point of the respective pair of row lines and column lines. The results of such an evaluation technique are particularly good if only a small proportion of the sensor arrays which are arranged essentially in matrix form supply a signal and the greater the number of data which are taken into account in the correlation calculation. In other words, illustratively, a two-dimensional image of a potential distribution on the sensor arrays of a sensor arrangement is not determined by progressive read-out of the individual matrix elements, as in accordance with the prior art, but rather by backcalculating the image from the accumulative current flows of the row lines and column lines of the matrix-type sensor arrangement. As a result, the favorable properties of a Fourier transformation are used according to the invention. The correlation calculations afford the further advantage of largely eliminating noise as an uncorrelated signal in the correlation calculation, so that the evaluation technique according to the invention results in higher robustness in respect of errors and an improved detection sensitivity. It should be noted that the transformation used for the evaluation need not necessarily be a Fourier transformation. Generally, it is possible to use any desired suitable spectral transformation (e.g., Laplace transformation, discrete sine transformation [DSC], discrete cosine transformation [DST]).

In accordance with another development, the decoding device is set up in such a way that, in order to determine whether a sensor signal is present at a sensor element, use is made of at least one accumulative current flow of at least one adjacent row line and/or of at least one adjacent column line.

"Adjacent" in the sense of the nomenclature used does not necessarily mean directly neighboring. Illustratively, during the evaluation of a sensor array arranged in a crossover region between a row line and a column line, use is made not only of the accumulative current flows of the two row and column lines arranged in said crossover region, but also optionally of the accumulative current flows of the other row lines arranged directly at this row line or in a manner separated by at least one row line. Moreover, it is possible to use not only the column line arranged in the crossover region, but also the further column lines directly adjoining it, or column lines which are arranged at a predetermined distance from the column line under consideration. In order to determine the sensor signal of a specific sensor array having the indices ij in the matrix-type sensor arrangement, use is made not only of accumulative current flows of the relevant column j and row i, but additionally of information from other columns l≠j and rows k≠i. This is advantageous particularly when a considerable proportion of the sensor arrays of the matrix-type sensor arrangement have a signal at a specific instant, i.e., when a plurality of sensor elements along a row or along a column simultaneously have a sensor signal. On account of the crosswise superposition of the individual sensor signals which are temporally and spatially superposed, there is then not only a dependence between precisely one row and one column signal (as assumed previously), rather these dependencies then extend over a group of active row and column lines. These interdependencies are taken into account in accordance with this refinement in order to be able to carry out a further improved identification and localization of the active sensor arrays. This concept achieves a greater tolerance with respect to noise and parameter fluctuations of the sensors and also with respect to the simultaneous activity of a plurality of sensors. The only prerequisite is that the signals are shifted at least slightly relative to one another or differ in their spectral contributions.

Preferably, the decoding device is set up in such a way that, in order to determine whether a sensor signal is present at a sensor element, use is made of at least one predetermined temporal and/or spatial reference signal. The decoding device of the sensor arrangement according to the invention may furthermore be set up in such a way that, in order to determine whether a sensor signal is present at a sensor element, the at least one predetermined temporal and/or spatial reference signal is adapted to the detected signal.

By way of example, a neuron (nerve cell), after a stimulation with an electrical signal, emits an electrical signal to be detected and having a shape that is characteristic of this process. If use is made of knowledge about the expected temporal and/or spatial shape of the signal to be detected, then it is possible to use this knowledge in order to separate superposed signals of different sensor arrays along individual rows or columns from one another. Signal profiles, which may be contained as a temporal or spatial reference signal in the decoding device, are known for many other biological or physical-technical systems. As a result, in the case of a possible overlapping of signals, i.e., in the case of simultaneous activity of a plurality of sensors along a row or column line, a further concept is provided for separating these signals from one another.

Preferably, the decoding device of the sensor arrangement according to the invention is set up in such a way that, in order to determine whether a sensor signal is present at a sensor element, at least two temporal and/or spatial reference signals are adapted to the detected signal.

The utilization of prior knowledge about the probable profile of the signals can be supplemented to the effect that superpositions of reference signals are also taken into account during the detection process. In other words, the adaptation of a predetermined temporal and/or spatial reference signal to a detected signal may also be effected using a plurality of reference signals. In this case, the decoding device also includes in the evaluation of the from the current signals of the row and column line the fact that a plurality of sensor signals are present simultaneously at a sensor array.

The sensor arrangement of the invention may furthermore be set up in such a way that, in order to determine whether a sensor signal is present at a sensor element at a second instant, use is made of a predetermined item of reference information about sensor signals at a first instant, which first instant temporally precedes the second instant.

In particular, the decoding device may be configured as a maximum likelihood sequence estimation decoder or as a maximum a posteriori decoder.

In accordance with the development described, the determination of those sensor arrays at which a sensor signal is present is carried out using previously known information about the probable profile of the signals, i.e., on the basis of known reference information. This may be effected using statistical methods known from the prior art, such as, by way of example, the maximum likelihood sequence estimation method, the maximum a posteriori method, or other methods suitable for this. The maximum likelihood sequence estimation method generally constitutes an estimation method for given statistics for determining parameters from a given sample of a random variable, in accordance with this method the values of the parameters being determined in such a way that a so-called "likelihood function" takes on a maximum. Illustratively, in the maximum likelihood sequence estimation method, the likeliest development of a system is determined on the basis of initial or boundary conditions. In a so-called trellis diagram, which represents different possible states of the system at different instants, that path of system states is determined which has the best correspondence with a detected sequence. Methods such as the maximum likelihood sequence estimation method or the maximum a posteriori method can contribute to carrying out, from a given sequence of samples, an estimation for a decomposition into different pattern signals. Using the methods described, it is possible to separate superposed pattern signals from one another if they are shifted only at least one sampling interval relative to one another. In the case of the sensor arrangement according to the invention, it suffices, therefore, for superposed signals to be shifted by at least one sensor array relative to one another. In particular, it should be pointed out that the pattern signals do not have to be known exactly from the outset. An adaptation of the pattern signals to the signals that are actually generated is possible. The methods described make it possible to reconstruct individual signals from a sensor signal formed from superposed individual signals.

In accordance with a further refinement of the sensor arrangement according to the invention, said sensor arrangement may have a voltage source, which is coupled to at least a portion of the row lines and of the column lines in such a way that a predetermined potential difference is provided for at least a portion of the coupling devices.

By way of example, a first reference potential (for example a supply voltage $V_{dd}$) may be applied to at least a portion of the column lines and at least a portion of the row lines are connected to a second reference potential (for example a lower reference potential $V_{ss}$ such as the ground potential). If the same electrical voltage is present at each of the coupling devices in crossover regions between the row and column lines to which the reference potentials described are applied, then the same quiescent current flows through each coupling device. A sensor event modulates the voltage at the coupling element and thus the current flow, which therefore represents a direct measure of the sensor events at the sensor element coupled to the respective coupling device.

Preferably, at least one coupling device is a current source controlled by the associated sensor element or a resistor controlled by the associated sensor element.

In other words, the electric current flow through a coupling device, in the case where the coupling device is configured as a current source controlled by the associated sensor element, depends on the presence or absence of a sensor event at the sensor element. The electrical resistance of the coupling device may also depend in a characteristic manner on whether or not a sensor event takes place at the assigned sensor element. In the case of such a variable resistance, the current through the coupling device for a fixed voltage between the assigned row and column lines is a direct measure of the sensor events effected at the sensor element. Designing the coupling device as a current source controlled by the associated sensor element or a resistor controlled by the associated sensor element enables the coupling devices to be realized in a manner exhibiting little complexity.

Preferably, at least one coupling device has a detection transistor having a first source/drain terminal coupled to one of the row lines, having a second source/drain terminal coupled to one of the column lines, and having a gate terminal coupled to the sensor element assigned to the coupling device.

Illustratively, the conductivity of the gate region of the detection transistor, preferably a MOS transistor, is influenced by whether or not a sensor event takes place at the assigned sensor element. If this is the case, i.e., if, by way of example, electrically charged particles (for example sodium and potassium ions) are brought into direct proximity to the sensor element from a neuron on the sensor element via ion channels, then these electrically charged particles alter the quantity of charge on the gate terminal of the detection transistor, thereby characteristically influencing the electrical conductivity of the channel region between the two source/drain terminals of the detection transistor. As a result, the current flow through the coupling device is influenced characteristically, so that the respective coupling device makes an altered contribution to the accumulative current flow of the respective row or column line. The configuration of the coupling device as a detection transistor constitutes a space-saving realization which exhibits little complexity and enables a cost-effective production and a high integration density of sensor arrays. The simple circuitry realization of the sensor arrays of the sensor arrangement according to the invention means that the cells can be made very small, which permits a high spatial resolution of the sensor.

Furthermore, at least one coupling device of the sensor arrangement according to the invention may have a calibration device for calibrating the coupling device.

The semiconductor-technological components of a sensor array are generally integrated components, such as MOS transistors, for example. Since these integrated components within a sensor array are usually made very small in order to achieve a high spatial resolution, a statistical variation of their electrical parameters (for example threshold voltages in the case of a MOSFET) occurs on account of fluctuations in the process implementation during the production method.

The deviation of the threshold voltages and other parameters may be compensated for for example by performing a calibration for example with the aid of a data table. For this purpose, an electric reference signal is in each case applied to individual sensor arrays of the matrix-type sensor arrangement, and the measured current intensities of the corresponding sensor elements are stored for instance in a table. During measurement operation, this table, which may be integrated as a database in the decoding device, serves for converting possibly erroneous measured values. This corresponds to a calibration.

As an alternative, the calibration device has a calibration transistor having a first source/drain terminal coupled to the row line, having a second source/drain terminal coupled to the gate terminal of the detection transistor and also to a capacitor coupled to the assigned sensor element, and having a gate terminal coupled to a further column line, it being possible for an electrical calibration voltage to be applied to the gate terminal of the calibration transistor by means of the further column line.

In accordance with the circuitry interconnection described, which requires a further transistor, namely the calibration transistor, and a capacitor compared with the above-described simple configuration of the coupling device as a detection transistor, the deviation of a parameter, such as, for example, the threshold voltage of the detection transistor, can be compensated for by a procedure in which an electrical potential is applied to the further column line, the calibration transistor consequently turns on and a node between the capacitor and the gate terminal of the detection transistor is charged to an electrical calibration potential. This calibration potential results from an electric current which is impressed in the row line and flows away into the column line through the detection transistor, acting as a diode. If the calibration transistor is turned off again because the voltage applied to the further column line is switched off, an electrical potential remains on the gate terminal of the detection transistor, which electrical potential permits a correction of the threshold voltage of the respective detection transistor for each sensor array of the sensor arrangement. And therefore, the robustness of the sensor arrangement according to the invention with respect to errors is improved with the use of a calibration device having a calibration transistor and a capacitor. In particular, impressing a zero current also enables any desired coupling device to be deactivated. If the calibration transistor is in the on state and if no current (zero current) is impressed in the row line, then the potential at the gate terminal of the detection transistor is reduced to an extent such that the detection transistor is turned off and remains correspondingly deactivated after the calibration transistor is switched off. This means that the associated sensor array, independently of the signal of the connected sensor element, contributes no signal to the accumulative signal of the row and column lines. In particular, this sensor array also does not contribute to the noise signal on the affected row and column lines, for which reason the later analysis of the signals at the remaining, still active sensor arrays is simplified.

The noise power of all the activated sensor arrays accumulates on the respective row and column lines. In the case of an application of the sensor arrangement according to the invention for neural signals and the resultant geometrical and electrical boundary conditions, the dominant disturbance variable is often a 1/f noise signal generated in the detection transistor. The noise power of this disturbance variable increases as the active component area decreases. If a multiplicity of sensor arrays are then connected to a row or column line, all contribute to the noise signal on the accumulative line. By deactivating individual sensor arrays using the concept described previously, or else by using a suitable deactivation switch for example in the signal current path of the sensor array, it is possible to improve the signal-to-noise ratio on the accumulative lines and thus the analysis of the signals. The possibility of deactivating individual sensor arrays is advantageous in particular because often only few of the sensor elements are covered with neurons and can thus potentially supply a signal. Even if a sensor element is covered with a neuron, it is not ensured that the electrical coupling between cell membrane and sensor surface suffices for transmitting a signal into the coupling device. If all these sensor arrays are deactivated, it is thereby possible to significantly improve the signal-to-noise ratio on the accumulative lines.

Furthermore, at least one coupling device of the sensor arrangement according to the invention may have an amplifier element for amplifying the individual electric current flow of the coupling device. In particular, the amplifier element may have a bipolar transistor having a collector terminal coupled to the row line, an emitter terminal coupled to the column line, and a base terminal coupled to the second/drain terminal of the detection transistor.

The use of a bipolar transistor as amplifier element, the design of which, with conventional semiconductor-technological methods, is not very complicated and is therefore possible in a cost-effective manner, provides a high-performance amplifier element having small dimensions on the sensor array, which can be used to achieve a high amplification of the often small current flows. This makes it possible to increase the sensitivity of the sensor arrangement.

Preferably, at least a portion of the row lines and of the column lines have an amplifier device for amplifying the accumulative electric current flow flowing in the respective row line and column line.

At least one sensor element of the sensor arrangement may be an ion-sensitive field-effect transistor (ISFET).

The functionality of an ISFET is described above. An ISFET constitutes a sensor element which can be produced with a low outlay in a standardized semiconductor-technological method and has a high detection sensitivity.

It is also possible for at least one sensor element on the sensor arrangement to be a sensor which is sensitive to electromagnetic radiation.

A sensor which is sensitive to electromagnetic radiation, for example a photodiode or another photosensitive element, enables the sensor arrangement to be operated as an optical sensor with a high repetition rate. The sensor arrangement according to the invention generally has the advantage that no further requirements are made of the sensor element except that a sensor event is intended to bring about an electrical signal.

The sensor arrays of the sensor arrangement are preferably formed essentially in rectangular fashion.

In this case, the sensor arrays are preferably arranged in matrix form. The column and row lines may be formed orthogonally with respect to one another along the edges of the rectangular sensor arrays. In other words, the row lines and the column lines of the sensor arrangement according to the invention may form essentially a right angle with one another.

In accordance with an alternative refinement of the sensor arrangement according to the invention, the sensor arrays are formed essentially in honeycomb-shaped fashion. In this case, honeycomb-shaped denotes a configuration of the sensor arrays in which the sensor arrays are hexagonal with pairs of parallel sides, furthermore preferably with 120° angles at each corner of the hexagon.

In the case of a honeycomb-shaped configuration of the sensor arrays, the row lines may form an angle of 60° with the column lines, and different column lines may either be parallel to one another or form an angle of 60° with one another.

The use of honeycomb-shaped sensor arrays achieves a particularly high integration density of sensor arrays, thereby achieving a high spatial resolution of the sensor arrangement.

Preferably, the sensor arrangement is divided into at least two regions that can be operated independently of one another, the sensor arrangement being set up in such a way that it is possible to predetermine which of the at least two regions are operated in a specific operation state. In this case, the regions may be arranged such that they are spatially directly neighboring (e.g., halves, quadrants) or be interleaved in one another, for example in such a way that, in the case of an orthogonal arrangement of sensor arrays, the coupling devices are connected for example in chessboard-like fashion to one or the other system of column and row lines.

The matrix-type sensor arrangement can thus be divided into different segments (for example into four quadrants) in order to increase the measurement accuracy on account of reduced line capacitances. By way of example, if it is known that sensor events cannot occur in a region of the sensor arrangement (for example because no neurons are grown in this region) then it is necessary only to examine the remaining region of the sensor arrangement, on which sensor events can take place. The supply of the unused region with supply voltages is therefore obviated. Furthermore, signals are to be evaluated only from that region in which sensor signals can occur. Moreover, for specific applications it may suffice to use only a partial region of the surface of the sensor arrangement which is smaller than the total surface of the sensor arrangement. In this case, the desired partial region can be connected in, which enables a particularly fast and not very complicated determination of the sensor events of the sensor arrays arranged on the partial region.

Exemplary embodiments of the invention are illustrated in the figures and are explained in more detail below.

BRIEF DESCRIPTION OF THE DRAWINGS

FIG. 3 shows a sensor arrangement in accordance with a second exemplary embodiment of the invention, FIG. 4A shows a sensor array of a sensor arrangement in accordance with a first exemplary embodiment of the invention, FIG. 4B shows a sensor array of a sensor arrangement in accordance with a second exemplary embodiment of the invention, FIG. 5A shows a sensor array of a sensor arrangement in accordance with a third exemplary embodiment of the invention, FIG. 5B shows a sensor array of a sensor arrangement in accordance with a fourth exemplary embodiment of the invention, FIG. 5C shows a sensor array of a sensor arrangement in accordance with a fifth exemplary embodiment of the invention, FIG. 5D shows a sensor array of a sensor arrangement in accordance with a sixth exemplary embodiment of the invention, FIG. 6 shows a schematic view of a sensor arrangement according to the invention, which is partly covered with neurons, in accordance with the second exemplary embodiment of the sensor arrangement according to the invention as shown in FIG. 3, FIG. 7 shows a sensor arrangement in accordance with a third exemplary embodiment of the invention, FIG. 8 shows a maximum likelihood sequence estimation decoder of the sensor arrangement in accordance with a first exemplary embodiment of the invention as shown in FIG. 7, FIG. 9 shows a trellis diagram.

DETAILED DESCRIPTION OF THE PREFERRED MODE OF THE INVENTION

A description is given below, referring to FIG. 2, of a sensor arrangement in accordance with a first exemplary embodiment of the invention.

Figure 1A:
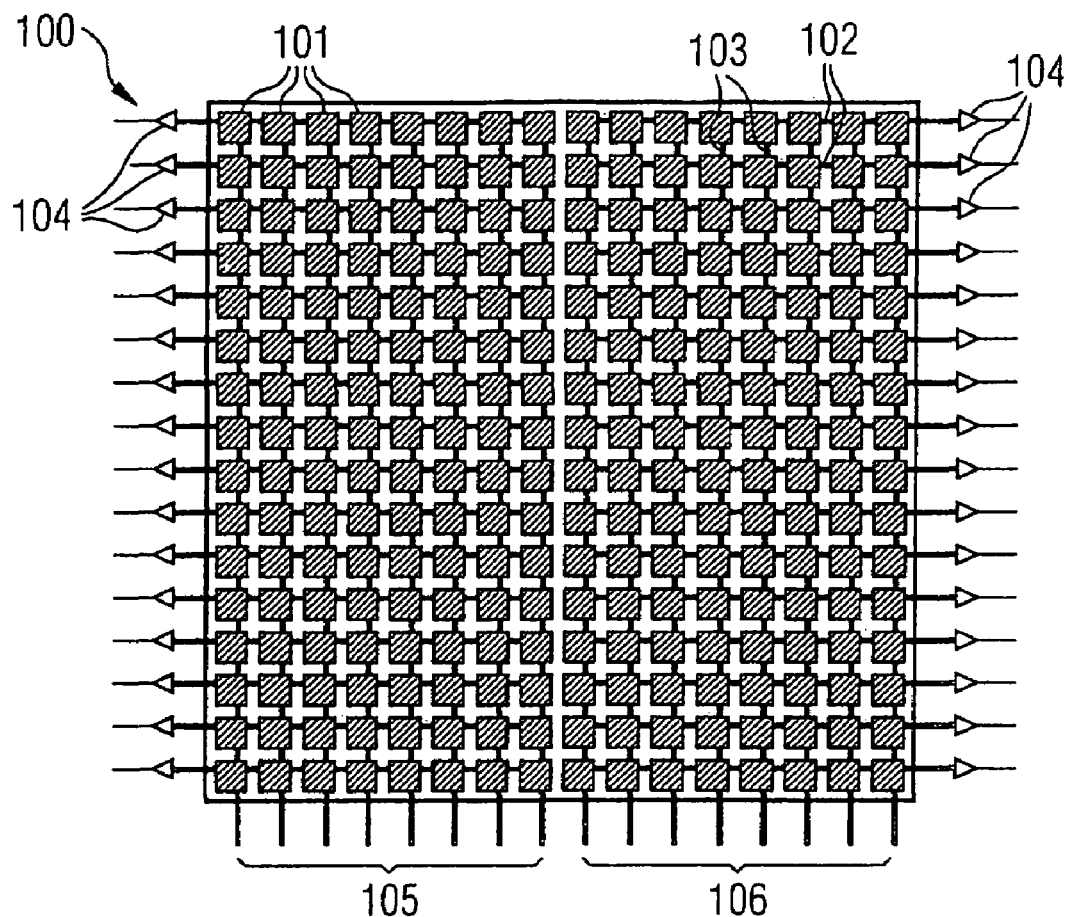
FIG. 1A shows a sensor arrangement in accordance with the prior art.
Figure 1B:
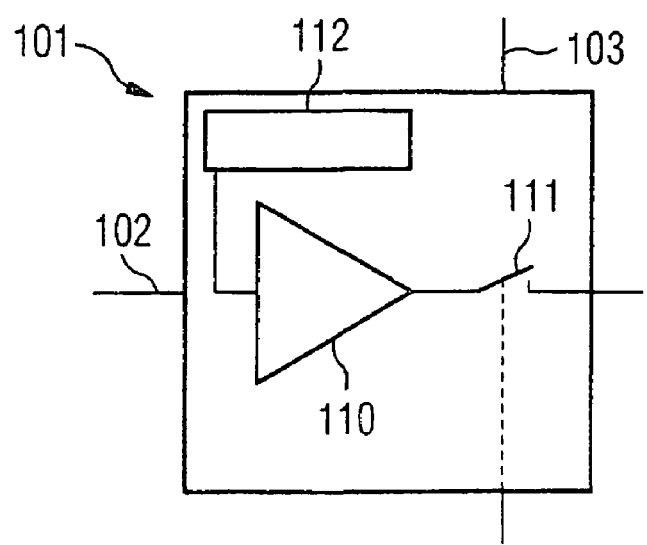
FIG. 1B shows a sensor electrode of the sensor arrangement in accordance with the prior art as shown in FIG. 1A.
Figure 2:
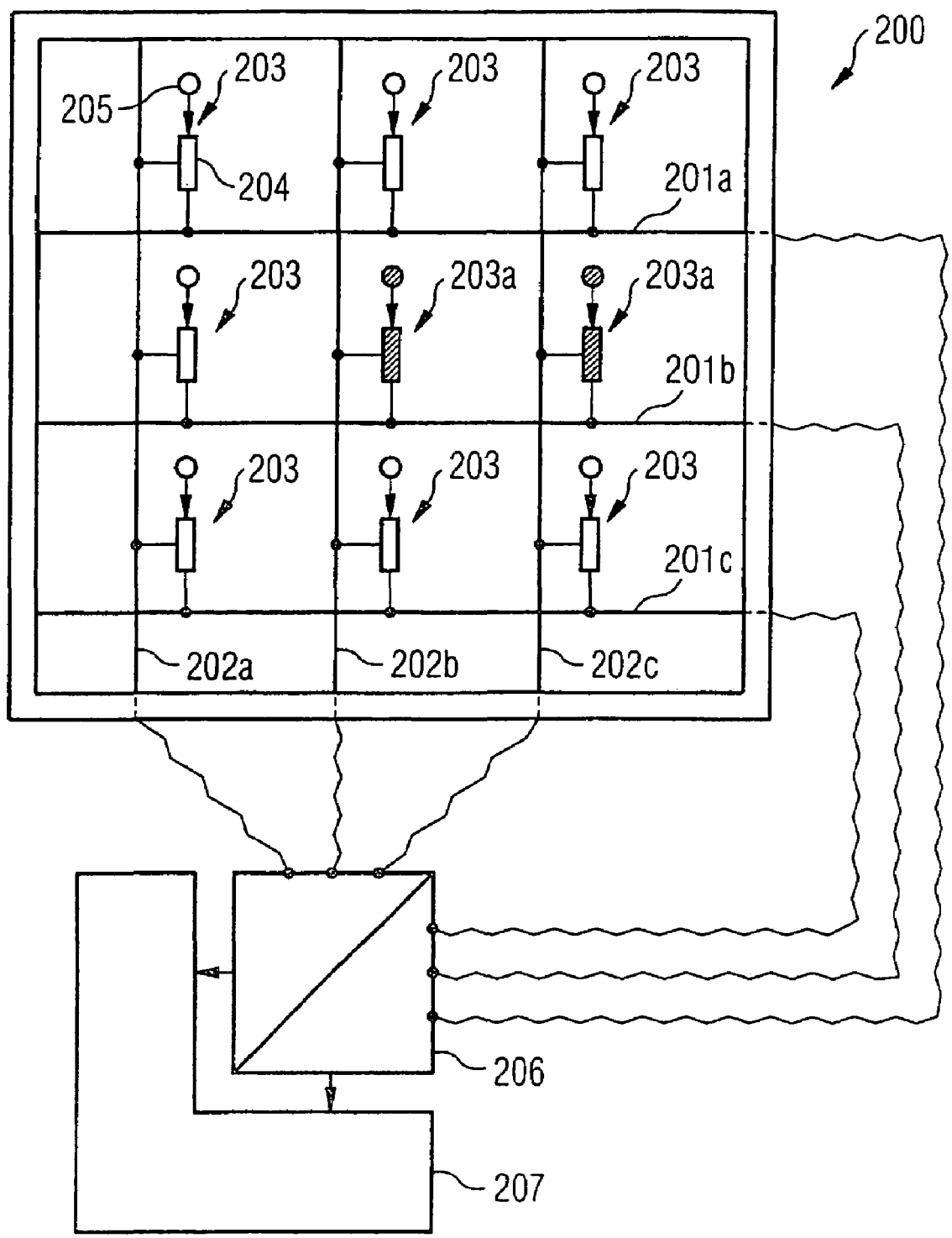
FIG. 2 shows a sensor arrangement in accordance with a first exemplary embodiment of the invention.

The sensor arrangement 200 shown in FIG. 2 has three row lines 201a, 201b, 201c arranged in a horizontal direction, three column lines 202a, 202b, 202c arranged in a vertical direction, and nine sensor arrays 203 arranged in the crossover regions between the three row lines 201a, 201b, 201c and column lines 202a, 202b, 202c, with a coupling device 204 for electrically coupling a respective row line 201a, 201b or 201c to a respective column line 202a, 202b or 202c and with a sensor element 205 assigned to the coupling device 204, the sensor element 205 being set up in such a way that the sensor element 205 influences the electric current flow through the assigned coupling device 204. Furthermore, the sensor arrangement 200 has a means 206 which is electrically coupled to a respective end section of the row lines 201a, 201b, 201c and of the column lines 202a, 202b, 202c and serves for detecting a respective accumulative current flow from the individual electric current flows provided by the sensor arrays 203 of the respective row and column lines. The sensor arrangement 200 furthermore has a decoding device 207, which is coupled to the row lines 201a, 201b, 201c and the column lines 202a, 202b, 202c and is set up in such a way that the activated sensor elements 203a at which a sensor signal is present can be determined from the accumulative electric current flows, which can be fed to the decoding device 207 via the row lines 201a, 201b, 201c and the column lines 202a, 202b, 202c.

The two activated sensor arrays 203a situated in the crossover regions between the second row 201b and the second and third columns 202b, 202c are emphasized visually in FIG. 2.

These sensor arrays 203a are those in which a sensor event takes place at the sensor element 205, on account of which the sensor element 205 characteristically influences the current flow through the coupling device 204. A voltage source (not shown in FIG. 2) provides a predetermined potential difference between each of the row lines 201a, 201b, 201c and each of the column lines 202a, 202b, 202c. Given this fixed potential difference, the current flow through the coupling devices 204 of the sensor arrays 203 is characteristically influenced by the sensor events at the assigned sensor elements 205. Illustratively, a greatly altered current flow can be detected particularly at the second row line 201b, since two of three sensor arrays 203 to which the row line 201b is coupled have an altered electric current flow on account of a sensor event. The second and third column lines 202b, 202c also have an (albeit less greatly) altered current flow since in each case one of three sensor arrays 203 coupled to said column lines 202b, 202c has an altered current flow. As shown schematically in FIG. 2, the accumulative current flows along the row lines 201a to 201c and the column lines 202a to 202c are provided to the means 206 for detecting accumulative current flows, which in turn provides the accumulative current flows detected to the decoding device 207. It can clearly be understood that, when examining the correlation of the accumulative currents of a respective row line with a respective column line, it is possible to determine which sensor arrays 203a are activated.

The decoding device 207 of the sensor arrangement 200 is set up in such a way that information about those sensor elements 205 at which a sensor signal is possibly present can be determined by carrying out a Fourier transformation of the time-dependent accumulative current flows of the row lines and of the column lines; multiplying together in pairs the Fourier-transformed accumulative current flows of the row lines and of the column lines; carrying out an inverse Fourier transformation with the accumulative current flows multiplied together in pairs.

Illustratively, pairwise cross-correlations of row and column lines are calculated. The sensor signal of a specific sensor element 205 $s_{ij}$ is determined by calculating pairwise cross-correlations of the time-dependent accumulative current flows of all the columns j with all the rows i. The correlation calculations using the mathematical operation of Fourier transformation and inverse Fourier transformation from the time domain to the frequency domain make it possible to determine the time-dependent signals of the individual sensor arrays 203. This is possible in particular because the electric current which flows through a coupling device 204 occurs in correlated fashion in the associated row line and also in the associated column line. In other words, a sensor event at a sensor element 205 of an activated sensor array 203a influences both the row line coupled thereto and the column line coupled thereto. It is an advantageous property of Fourier transformation that uncorrelated signals, that is to say noise signals and the like, are at least partly eliminated during the correlation calculation. With the aid of the Fourier transformation method described, it is therefore possible to determine the activated sensor arrays 203a from the accumulative current signals of the three row lines 201a to 201c and the accumulative current flows of the three column lines 202a to 202c, that is to say from a total of 3+3=6 accumulative current signals. By contrast, methods known from the prior art require the signals of the 3*3=9 sensor arrays 203 to be read out separately and, therefore, nine signals to be detected. (In the case of apparatuses in accordance with the prior art, both currents and voltages can be derived as information-carrying variable from the sensor arrangement.) The invention therefore reduces the number of current signals to be detected, which enables an increased evaluation speed and, for a predetermined maximum read-out rate an increase in the number of sensor arrays 203 of a sensor arrangement 200. It is pointed out that the numerical advantage is higher, the higher the number of row and column lines. In the general case, the determination of nm current signals as required from the prior art given m columns and n rows is reduced to m+n accumulative current signals which are to be detected according to the invention.

FIG. 3 shows a sensor arrangement in accordance with a second preferred exemplary embodiment of the invention.

The sensor arrangement 300 is constructed similarly to the sensor arrangement 200 described with reference to FIG. 2. In particular, the sensor arrangement 300 has sixteen row lines 301 and sixteen column rows 302. According to the invention, therefore, 32 accumulative current signals are to be detected, whereas 256 current signals of the 256 sensor arrays 304 would have to be detected in the case of a concept known from the prior art. In the case of the sensor arrangement 300 shown in FIG. 3, the sensor arrays 304 are formed in rectangular fashion. The row lines 301 and the column lines 302 form a right angle with one another. The sensor arrangement 300 is divided into four partial regions 303a, 303b, 303c, 303d that can be operated independently of one another, the sensor arrangement 300 being set up in such a way that it is possible to predetermine which of the four partial regions 303a to 303d are operated. The arrangement of the four partial regions 303a to 303d within the sensor arrangement 300 is shown in the schematic sketch 300a in FIG. 3. Each row line 301 and each column line 302 of the sensor arrangement 300 has an amplifier device 305 for amplifying the accumulative electric current flow flowing in the respective row line 301 and column line 302.

Possibilities for the detailed construction of the sensor arrays 304 are explained below on the basis of preferred exemplary embodiments with reference to FIG. 4A to FIG. 5B.

FIG. 4A shows a sensor array 400 in accordance with a first exemplary embodiment of the invention.

The sensor array 400 is arranged in a crossover region between a row line 401 and a column line 402. The row line 401 is coupled to the column line 402 via a coupling device 403 via two electrical crossover points. The coupling device 403 is designed as a resistor that can be controlled by a sensor element 404. In other words, a sensor event at the sensor element 404 has the effect of influencing the electrical resistance of the coupling device 403 in a characteristic manner. The sensor array 400 is a square having a side length d. In order to achieve an integration density of sensor arrays 400 in a sensor arrangement that is high enough for neurobiological purposes, the edge length d of the square sensor array 400 is preferably chosen to be less than 20 m.

FIG. 4b shows a sensor array 410 in accordance with a second exemplary embodiment of the invention.

The sensor array 410 is arranged in a crossover region between a row line 411 and a column line 412. The sensor array 410 has a coupling device 413, by means of which the row line 411 is coupled to the column line 412 via two electrical coupling points. In accordance with the exemplary embodiment shown in FIG. 4B, the coupling device 413 is designed as a current source controlled by the sensor element 414. In other words, a sensor event at the sensor element 414 has the effect of influencing the electric current of the controlled current source 413 in a characteristic manner.

Thus, a controlled resistor or a controlled current source having a linear or nonlinear characteristic curve is provided as coupling device 403 or 413 within a sensor array 400 or 410, respectively. What is essential is that, with the aid of a suitable circuitry interconnection, a current flow is branched from a row line into a column line, which current flow is characteristically influenced by a sensor event.

FIG. 5A shows a sensor array 500 in accordance with a third exemplary embodiment of the invention.

The sensor array 500 shown in FIG. 5A is arranged in a crossover region between a row line 501 and a column line 502. By means of a coupling device designed as a detection transistor 503, the row line 501 is coupled to the column line 502 via two electrical crossover points. The detection transistor 503 has a first source/drain terminal coupled to the row line 501, a second source/drain terminal coupled to the column line 502, and a gate terminal coupled to the sensor element 504. The length l of a side of the sensor array 500 formed in square fashion is preferably less than 20·m in order to achieve a sufficiently high spatial resolution.

A constant electrical voltage is applied to the row line 501 and the column line 502. If a sensor event takes place at the sensor element 504, in the case of which electrically charged particles characteristically influence the potential of the gate terminal of the detection transistor 503, then the conductivity of the conductive channel between the two source/drain terminals of the detection transistor 503 is influenced on account of the sensor event. Therefore, the electric current flow between the first and second source/drain regions of the detection transistor 503 is a measure of the sensor event that has taken place at the sensor element 504. In other words, prior to a sensor event the sensor element 504 is brought to a predetermined electrical potential by means of a suitable measure, so that, between the two source/drain terminals of the detection transistor 503, a quiescent electric current flows from the column line 502 into the row line 501. As the electrical potential of the gate terminal is influenced, for example because a neuron coupled to the sensor element 504 emits an electrical pulse, the shunt current between the row line 501 and the column line 502 is thus altered on account of the altered electrical conductivity of the detection transistor 503.

Referring to FIG. 5B, a description is given below of a fourth exemplary embodiment of a sensor array of a sensor arrangement according to the invention.

The sensor array 510 shown in FIG. 5B is arranged in a crossover region between a row line 511 and a first column line 512*a*. As in the case of the sensor array 500, the sensor array 510 also has a detection transistor 513. Furthermore, the coupling device of the sensor array 510 has a calibration device for calibrating the coupling device. In accordance with the exemplary embodiment shown in FIG. 5B, the calibration device has a calibration transistor 515 having a first source/drain terminal coupled to the row line 511, having a second source/drain terminal coupled to the gate terminal of the detection transistor 513 and also to a capacitor 516 coupled to the assigned sensor element 514, and having a gate terminal coupled to a second column line 512*b*, it being possible for an electrical calibration voltage to be applied to the gate terminal of the calibration transistor 515 by means of the second column line 512*b*.

The calibration device of the sensor array 510 is set up in such a way that, by means of suitable control of the voltage signals on the first and second column lines 512*a*, 512*b* and also on the row line 511, it is possible to compensate for a deviation of parameters of the detection transistor 513 from parameters of detection transistors of other sensor arrays of the sensor arrangement according to the invention on account of nonuniformities during the production method. In particular, a statistical variation of the value of the threshold voltage of the detection transistors 513 of different sensor arrays of a sensor arrangement about a mean value may occur. The deviation of the threshold voltage between different sensor arrays can be compensated for by bringing the second column line 512*b* to an electrical potential such that the calibration transistor 515 is in the on state and the electrical node between the capacitor 516 and the gate terminal of the detection transistor 513 is brought to a calibration potential. The calibration potential is determined by the electric current which is fed into the row line 511 and flows through the detection transistor 513, connected as a diode. If the calibration transistor 515 is turned off again, an electrical voltage remains on the gate terminal of the detection transistor 513, which electrical voltage enables a correction of the different threshold voltages of different detection transistors 513 of different sensor arrays of a sensor arrangement.

It should be pointed out that the side length s of the square sensor array 510 is typically between approximately 1·m and approximately 10·m.

A description is given below, referring to FIG. 5C of a fifth exemplary embodiment of a sensor array of the sensor arrangement according to the invention.

Like the sensor array 510, the sensor array 520 has the following components interconnected in a manner analogous to that shown in FIG. 5D: a row line 521, a first and a second column line 522*a*, 522*b*, a detection transistor 523, a sensor element 524, a calibration transistor 525 and a capacitor 526. Furthermore, the sensor array 520 has an amplifier element for amplifying the individual electric current flow of the coupling device of the sensor array 520. Said amplifier element is in the form of a bipolar transistor 527 having a collector terminal coupled to the row line 521, having an emitter terminal coupled to the first column line 522*a*, and having a base terminal coupled to the second source/drain region of the detection transistor 523. The electric current between the row line 521 and the first column line 522*a* is greatly amplified on account of the current-amplifying effect of the bipolar transistor 527. An increased sensitivity of the entire sensor arrangement is thereby achieved.

FIG. 5D shows a sensor array 530 in accordance with a sixth exemplary embodiment of the invention.

The sensor array 530 is formed in honeycomb-shaped fashion. A row line 531 in each case forms an angle of 60° with a first column line 532*a* and with a second column line 532*b*, the two column lines 532*a* and 532*b* also forming an angle of 60° with one another. The sensor array 530 has a first detection transistor 533*a* and a second detection transistor 533*b*. The gate terminals of the two detection transistors 533*a*, 533*b* are coupled to a sensor element 534. The first source/drain terminal of the first detection transistor 533*a* and the first source/drain terminal of the second detection transistor 533*b* are coupled to the row line 531. The second source/drain terminal of the first detection transistor 533*a* is coupled to the first column line 532*a*, whereas the second source/drain terminal of the second detection transistor 533*b* is coupled to the second column line 532*b*.

If a sensor event takes place at the sensor element 534, as a result of which electrical charge carriers are generated at the sensor element 534, then the conductivity of the channel regions of the first and second detection transistors 533*a*, 533*b* thereby changes in a characteristic manner. This results in a change on the one hand in the electric current flow from the row line 531 into the first column line 532*a* and on the other hand in the current flow from the row line 531 into the second column line 532*b*. In accordance with the concept shown in FIG. 5D, too, the accumulative current flows in the column lines and in the row lines are detected in edge regions of an arrangement of a multiplicity of the sensor arrays 530 and the signals of the individual sensor arrays 530 are calculated by means of the temporal correlation of the accumulative current flows.

Since, on account of the space-saving configuration of the sensor arrays shown with reference to FIG. 4A to FIG. 5D, the sensor arrays can be made small enough to achieve a high spatial resolution, the noise level in the individual current of a sensor array may take on a value which may be of the same order of magnitude as the actual signal current. Although the noise current flows of all of the connected sensor elements accumulate on the row lines and the column lines, this uncorrelated signal is omitted during correlation calculation, so that only the sensor signal and the noise signal of a single sensor array contribute to the calculated measurement signal of said sensor array.

A description is given below, referring to FIG. 6, of the sensor arrangement 300 as shown in FIG. 3 in an active operating state.

In accordance with the operating state of the sensor arrangement 300 as shown in FIG. 6, a first neuron 604, a second neuron 605 and a third neuron 606 are arranged on the matrix-type arrangement of sensor arrays 304. In accordance with the preferred exemplary embodiment, the sensor arrays 304 are electrically conductive electrodes (e.g., Au, Pt, Pd) which are coated with a dielectric (e.g., $SiO_2$, $Si_3N_4$) and are electrically operatively connected to an amplifier (e.g., MOS- FET). FIG. 6 furthermore shows a first projection 600, a second projection 601, a third projection 602 and a fourth projection 603 of the two-dimensional arrangement of neurons 604 to 606 on the matrix-type sensor arrangement 300. As described with reference to FIG. 3, the matrix-type sensor arrangement 300 is divided into four partial regions 303a to 303d each coupled to dedicated row and column lines, respectively. Therefore, the projections 600 to 603 in each case supply a two-dimensional mapping of the arrangement of neurons generating a sensor signal in the respective partial regions 303a to 303d. By way of example, the first neuron 604, which is essentially arranged in the second partial region 303b of the sensor arrangement 300, supplies a corresponding signal in the right-hand partial region of the first projection 600 in accordance with FIG. 6 and in the central region of the second projection 601. Since a small part of the first neuron 604 is also arranged in the third partial region 303c, a small signal of the first neuron 604 can be seen in the right-hand partial region of the third projection 602 in accordance with FIG. 6. In this way, each of the neurons 604 to 606 contributes to a signal in a respective part of the projections 600 to 603. The combined signals of the projections 600 to 603 supply information about the spatial arrangement of the neurons 604 to 606.

A description is given below, referring to FIG. 7, of a third preferred exemplary embodiment of the sensor arrangement according to the invention.

The sensor arrangement 700 shown in FIG. 7 has sixteen horizontally arranged row lines 701, sixteen vertically arranged column lines 702 and 256 sensor arrays 703 arranged in the crossover regions between the row lines 701 and the column lines 702. Each of the sensor arrays 703 is designed in the same way as the sensor array 500 shown in FIG. 5A. Electrically coupled means for detecting a respective accumulative current flow from the individual electric current flows provided by the sensor arrays 703 of the respective line 701, 702 are provided at the respective end sections of the row lines 701 and of the column lines 702. In accordance with the exemplary embodiment of the sensor arrangement 700 as shown in FIG. 7, said means are part of a decoding device 704 configured as a maximum likelihood sequence estimation decoder. The decoding device 704 coupled to the row lines 701 and the column lines 702 is set up in such a way that it determines, from at least a portion of the accumulative electric current flows, which can be fed to the decoding device 704 via the row lines 701 and the column lines 702, those sensor elements of the sensor arrays 703 at which a sensor signal is present.

Furthermore, each row line 701 and each column line 702 has an amplifier device 705 for amplification and optionally a sample/hold device (not shown) for temporally accurate storage of the accumulative electric current flow flowing in the respective row line 701 and column line 702.

Before the sensor arrangement 700 shown in FIG. 7 is described in more detail, reference is once again made to the sensor arrangement 300 shown in FIG. 6. The operation—described with reference to FIG. 6—of the sensor arrangement 300 for determining the spatial and temporal profile of sensor events by calculating pairwise cross-correlations yields very good results if, as shown in FIG. 6, only a small proportion of the sensor arrays supplies a sensor signal.

Referring to FIG. 6, a description is given of a development of the sensor arrangement according to the invention in which a decoding and therefore a determination of the profiles of the individual sensor signals are made possible even in the case of a high degree of overlapping of sensor signals of the individual sensor arrays or in the presence of a high degree of noise. It is thus ensured that, even when the disturbance influences described are present, the individual sensor signals can be reconstructed from the accumulative current flows of the row and column lines. This is done on the basis of information about possible signal profiles which is known beforehand at the beginning of the decoding. Characteristic signal profiles are known for many technical processes in the natural sciences.

In the case of the sensor arrangement 300, sensor arrays 304 arranged in matrix form are connected to common row and column lines 301, 302. The individual current flows of all the connected sensor arrays accumulate on said common row and column lines 301, 302. The determination of the sensor signals of each individual sensor array is made possible by calculating pairwise cross-correlations of the time-dependent accumulative current flows of all the columns with all the rows using a Fourier transformation and an inverse Fourier transformation. This concept makes it possible, in the case of simultaneous activity of only one sensor array, to accurately locate the latter even in the presence of noise signals from the remaining sensor arrays. The concept described is particularly advantageous in the case of sensor arrangements having a high number of rows and columns, in the case of which only a small proportion of the sensor arrays has a sensor event at a fixed point in time. It then suffices without an additional selection logic for the spatially resolved measurement of the signals to detect the accumulative current flows along the row lines and column lines and to determine the sensor signals of the sensor arrays computationally.

However, it can happen in practice that a plurality of sensor arrays simultaneously supply a sensor signal and that the sensor signals generated by them have similar or identical intensities. In accordance with the concept of the sensor arrangement 300, the signals generated by the sensor arrays are superposed both in rows and columns. Problems can arise if a plurality of sensor arrays are simultaneously active, whose individual current flows along the row and column lines are accumulated. It can then happen that the value of the cross-correlation does not always assume the maximum possible value for precisely one column and row signal, but rather, under certain circumstances, for other, superposed row and column signals with high intensity. An unambiguous detection of the individual sensor signals is at least made more difficult in these cases.

These difficulties are avoided in accordance with the concept shown in FIG. 7 by virtue of the decoding device 704 being configured as a maximum likelihood sequence estimation decoder. The functionality of the decoding device 704 is described below.

During the backcalculation of the sensor signals of the sensor arrays 703 from the accumulative current flows of the row lines 701 and of the column lines 702, in accordance with the functionality of the decoding device 704, with regard to a specific sensor array 703 in the i-th row and the j-th column of the matrix-type arrangement of sensor arrays 703, use is made not only of the information of the accumulative current flows of the i-th row and the j-th column, but additionally of information from other, preferably all other, columns $l \neq j$ and rows $k \neq i$. This is because, in the case of a superposition of individual, generally temporally superposed sensor signals, there is not only a dependence between precisely one accumulative current flow of a row line and a accumulative current flow of a column line, rather these dependencies extend over larger regions of active row lines and column lines. These interactions are included in the evaluation method carried out by the decoding device 704 in that accumulative current flows of row and column lines in whose crossover regions a sensor array 703 under consideration is not arranged are also included in the determination method. In other words, the decoding device 704 is set up in such a way that in order to determine whether a sensor signal is present at a sensor element, use is made of at least one accumulative current flow of at least one adjacent row line and/or of at least one adjacent column line.

Furthermore, the decoding device 704 has the functionality that, during the determination of the sensor arrays at which a sensor signal is present, account is taken of an expected curve shape of the signals which can be generated on account of physical boundary conditions in the individual sensor arrays. Thus, by way of example, nerve cells emit a signal having a characteristic curve shape as a reaction to an electrical excitation. If such boundary conditions are taken into account during the determination method, then the determination of those sensor arrays 703 at which a sensor signal is present can be carried out sufficiently reliably. Therefore, the decoding device 704 is set up in such a way that in order to determine whether a sensor signal is present at a sensor element, use is made of at least one predetermined temporal and/or spatial reference signal.

By using previously known information (for example with regard to expected curve shapes of signals), it is also possible to take account of the superposition of different signals with the signal shape of a reference signal. For this purpose, it is possible to use an algorithm which is set up in such a way that, from a detected signal composed of a plurality of individual signals, it decomposes this signal into the partial components. In particular, the maximum likelihood sequence estimation algorithm and the maximum a posteriori algorithm are suitable for this. As described above, the decoding device 704 is configured as a maximum likelihood sequence estimation decoder.

It must be emphasized that the pattern signals or reference signals do not have to be previously known in detail. The pattern or reference signals can be adapted to the signals that are actually determined. To summarize, therefore, the decoding device 704 has the functionality that in order to determine whether a sensor signal is present at a sensor element, the at least one predetermined temporal and/or spatial reference signal is adapted to the detected signal. Furthermore, the decoding device 704 is set up in such a way that in order to determine whether a sensor signal is present at a sensor element at a second instant, use is made of a predetermined item of reference information about sensor signals at a first instant, which first instant temporally precedes the second instant.

In other words, the decoding device 704 takes a decision about the activity of a sensor array taking account of at least one reference signal which characterizes an expected signal profile. Parameters of the reference signal are adapted to the actual signal profile and provided for further processing at an output 704a of the decoding device 704. Furthermore, the decoding device 704 is set up in such a way that a temporal and/or spatial superposition of a plurality of sensor signals can be included in the decision process. In the case of the decoding device 704, the maximum likelihood sequence estimation algorithm is used in the decision process.

As shown in FIG. 7, the decoding device 704 has the first output 704a and furthermore a second output 704b. The first output 704a is set up in such a way that reference signals (pattern signals) can be provided at said output. At the second output 704b, it is possible to provide data signals containing the information concerning the sensor arrays 703 at which a sensor event has with high probability taken place.

FIG. 8 shows the schematic construction of the decoding device 704. The decoding device 704 has a plurality of input interfaces 800. Each of the row lines 701 and each of the column lines 702 is respectively coupled to precisely one of the input interfaces 800 of the decoding device 704. A switch 801, which may be present in an open state and in a closed state, is in each case arranged between an end section of each row line 701 and of each column line 702, on the one hand, and the respectively assigned input interface 800 of the decoding device 704, on the other hand. In order to feed the accumulative current flow of a row line 701 and of a column line 702 to the decoding device 704 via the respectively assigned input interface, the switch 801 assigned to the respective line is closed. The accumulative current flows of the row lines 701 and of the column lines 702 which are fed to the decoding device 704 are evaluated in the decoding device 704, an estimation of the likeliest activity of the sensor arrays 703 being carried out using the maximum likelihood sequence estimation algorithm. The temporal sequence with which the individual switches 801 are successively opened and closed again depends on the bandwidth of the incoming signal and on the likelihood that more than one sensor array 703 generates the same signal profile in the same sampling interval. This likelihood increases proportionally to the length of the sample interval, assuming a uniform distribution. An increased sampling rate is therefore desirable and affords a possibility for system optimization.

Referring once again to FIG. 8, the functionality of the decoding device 704 may be summarized as follows. Given a closed switch 801, the decoding device 704 is provided with a accumulative current flow of the row line 701 and column line 702 assigned to the closed switch. As a result, the decoding device 704 is progressively provided with the accumulative current flows of all the row lines 701 and all the column lines 702. These accumulative current flows are coded signals which have a noise signal and are a mapping of the sensor events on the sensor arrays 703 of the sensor arrangement 700. On the basis of the functionality of the decoding device 704 configured as a maximum likelihood sequence estimation decoder, from the accumulative current flows a decision is taken computationally about the presence or absence of a sensor event at the sensor arrays 703 which, from all the calculated constellations, in accordance with the maximum likelihood sequence estimation method, correspond the most probably to the actual sensor events.

The trellis diagram 900 shown in FIG. 9 is described below.

The trellis diagram 900 is a state transition graph of a system to be described which is plotted along a time axis 901. States of the sensor arrays of the sensor arrangement according to the invention at different points in time are represented along the time axis 901. At a fixed point in time, for example at the instant $t_0$ shown in FIG. 9, possible states of the sensor arrangement, more precisely of the n m sensor arrays of the sensor arrangement, are represented orthogonally with respect to the time axis 901. In this case, m denotes the number of rows of the matrix-type arrangement of sensor arrays and n denotes the number of columns. The sensor array of the i-th row and j-th column of the matrix-type sensor arrangement is designated by $s_{ij}$. The states of the n·m-dimensional sensor arrangement can be described in a trellis diagram with $A^{(nmL)}$ states, where (A−1) denotes the number and (L+1) denotes the length of the pattern pulses (reference signals) $a_k$ relative to the sampling interval. The present output value of each of the n m sensor arrays $s_{ij}$ at a specific instant, for example $t_0$, depends on L earlier activity states, there being A different possibilities $a_0, a_1, \ldots, a_A$ (no activity or a pattern signal from (A−1) different ones).

Arrows 904 indicate possible transitions between trellis states at a first instant to 902 and trellis states at a second instant $t_1$ 903. Since the number of possible state changes, i.e., the number of changes in the activity pattern, of each sensor is restricted to at most A possibilities from one sampling interval to the next, a total of (A·n·m) possible state changes result in the trellis diagram 900. This corresponds to the number of possible states which proceed from each state and are indicated by the arrows 904. The number of possible transitions decreases if previously known information with regard to reference signals about the temporal/spatial profiles of the sensor signals is previously known and can be used.

A decoding device which operates on the basis of the trellis diagram 900 and is configured as a maximum likelihood sequence estimation decoder supplies an estimation about the state of the sensor array, i.e., the activity pattern of the individual sensor arrays, with respect to each sampling interval. The actual pattern sequences can be calculated from these data and from the original activity pattern. Said sequences may be used for another measurement or for a new evaluation of the present measurement (iteratively).

Illustratively, the maximum likelihood sequence estimation method is used to determine that path of trellis states 902, 903, . . . along the time axis 901 which corresponds to the likeliest signal profile.

A description is given below, referring to FIG. 10, of a sensor arrangement in accordance with a fourth exemplary embodiment of the invention.

Figure 10:
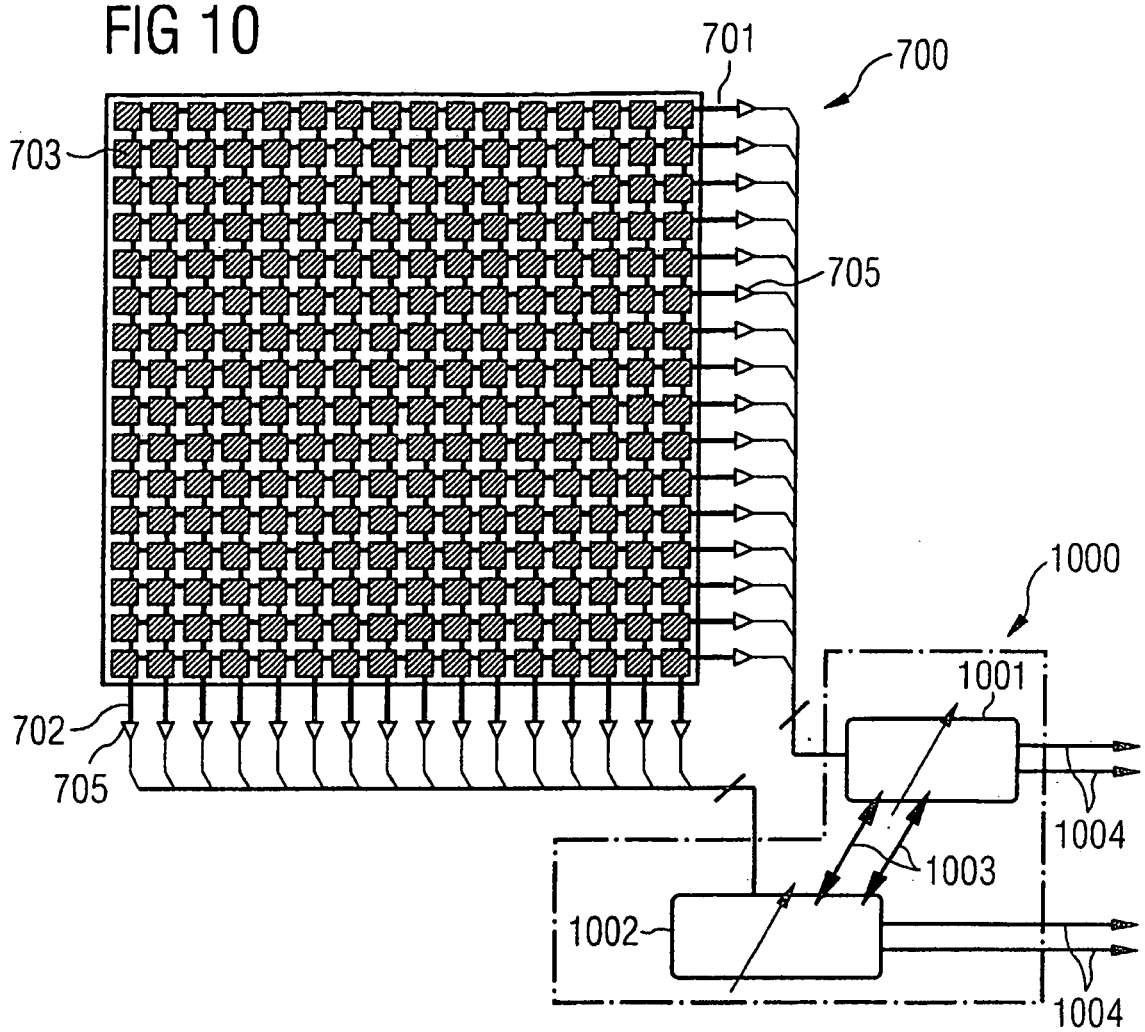
FIG. 10 shows a sensor arrangement in accordance with a fourth exemplary embodiment of the invention.

In a departure from the configuration shown in FIG. 7, the sensor arrangement 700 shown in FIG. 10 has a decoding device 1000. The decoding device 1000 is configured as a maximum likelihood sequence estimation decoder.

The decoding device 1000 is divided into a row decoding device 1001, to which the accumulative electric current flows of the row lines 701 can be fed, and a column decoding device 1002, to which the accumulative electric current flows of the column lines 72 can be fed. The row decoding device 1001 is set up in such a way that information about those sensor elements 703 at which a sensor signal is possibly present can be determined from the accumulative electric current flows of the row lines 701 independently of the accumulative current flows of the column lines 703. The column decoding device 1002 is set up in such a way that information about those sensor elements 703 at which a sensor signal is possibly present can be determined from the accumulative electric current flows of the column lines 702. The decoding device 1000 is furthermore set up in such a way that those sensor elements at which a sensor signal is present can be determined by means of joint evaluation of the information determined by the row decoding device 1001 and the column decoding device 1002.

In other words, the accumulative current flows of the row lines 701 are evaluated without the information about the accumulative current flows of the column lines 702 being taken into account in this evaluation process. Analogously, in the column decoding device 1002, the accumulative current flows of the column lines 702 are evaluated independently of the accumulative current flows of the row lines 701. This leads to a considerable numerical simplification.

The decoding device 1000 described has the advantage that the numerically very complicated joint evaluation of the accumulative current flows of the row and column lines in the case of sensor arrangements having a large number of sensor arrays is avoided. The functionality of the decoding device 1000 is based on a suboptimum iterative method for determining those sensor arrays 703 at which a sensor signal is present. In contrast to the decoding device 704 from FIG. 8, the accumulative current flows of the row lines 701 are decoded in the row decoding device 1001, on the one hand, and the accumulative current flows of the column lines 702 are decoded by means of the column decoding device 1002, initially independently of one another. Although the fundamental sequence of the algorithm on which this decoding is based corresponds to the method described above with reference to FIGS. 7-9, the trellis diagram in the case of the decoding device 1000 has in each case only $a^L$ states and correspondingly fewer transitions between trellis states at different points in time. Consequently, the decoding is faster and possible with a lower computational complexity. By finding simultaneous activation patterns of the sensors, it is possible to determine the position of the active sensor arrays 703 by adjustment of the row and column signals. Such an adjustment is symbolized by means of the arrows 1003 in FIG. 10. The output signals 1004 shown in FIG. 10 may have data about activated sensor arrays 703 and reference signals (pattern signals).

In the case of the decoding device 1000, too, it is possible for pattern sequences used to be adapted to sequences that are actually measured. After the transmission of the pattern signals, the detection process can be initiated anew with the same sensor data. However, use is then made of pattern signals which are already more suitable, since they have been adapted in the preceding step, so that this method improves the error tolerance with respect to the noise with each iteration step. The number of iteration steps can be predetermined according to the invention, so that the accuracy of the decoding method can be set by means of the selection of the number of iteration steps.

A description is given below, referring to FIG. 11, of the schematic construction of one configuration of the decoding device 1000.

Figure 11:
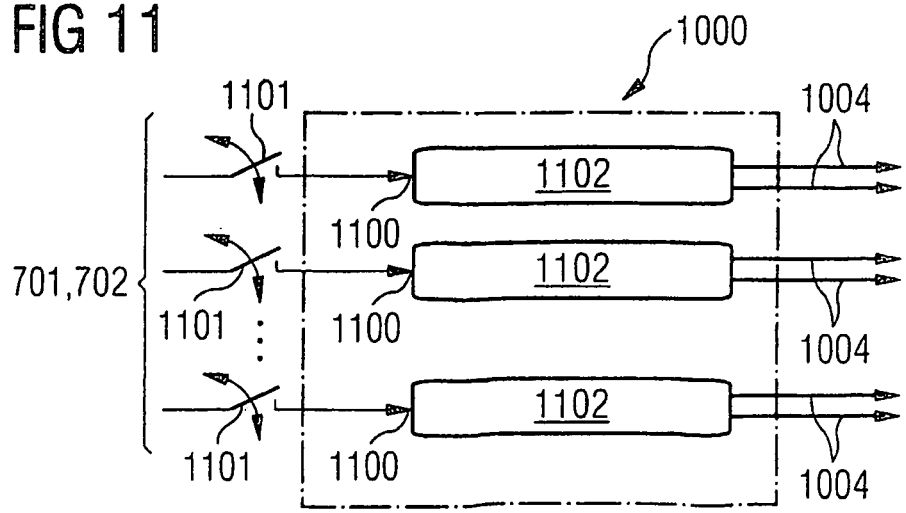
FIG. 11 shows a maximum likelihood sequence estimation decoder of the sensor arrangement in accordance with a second exemplary embodiment of the invention as shown in FIG. 10.

As shown in FIG. 11, the decoding device 1000 has n+m input interfaces 1100. A switch 1101 is arranged between a respective one of the input interfaces 1100 and an end section of the precisely one row and column line 701, 702 assigned to each input interface 1100. The decoding device 1000 is divided into n+m partial decoding devices 1102, each of which, in a scenario in which the respectively associated switch 1001 is closed, is coupled to one of the row lines 701 or column lines 702, so that the associated accumulative current flow can be fed to the respective input interface 1100. In other words, a respective accumulative current flow of one of the m row lines 701 or of the n column lines 702 can be provided to one of the partial decoding devices 1102. Therefore, m of the partial decoding devices 1102 form the row decoding device 1001, whereas m of the partial decoding devices 1102 form the column decoding device 1002. The accumulative current flows of the row lines 701 and the accumulative current flows of the column lines 702 are decoded independently of one another in the respective partial decoding devices 1102. The output signals 1004 having data about activated sensor arrays 703, are provided at the outputs of the decoding device 1000. Furthermore, the output signals 1004 may contain information about the reliability of the evaluation or pattern sequences.

What is claimed is:
1. A sensor arrangement comprising:
a plurality of row lines arranged in a first direction;
a plurality of column lines arranged in at least a second direction;
a plurality of sensor arrays arranged in crossover regions of the row lines and the column lines, each of the plurality of sensor arrays having:
at least one coupling device for electrically coupling a respective row line to a respective column line; and a sensor element assigned to the at least one coupling device, wherein the sensor element influences electric current flow through the at least one assigned coupling device;

a detector electrically coupled to a respective end section of at least a portion of the row lines and of at least a portion of the column lines, the detector detecting a respective accumulative current flow from the individual electrical current flows provided by the sensor arrays of the respective lines; and a decoding device coupled to the row lines and the column lines, the decoding device evaluating at least a portion of the accumulative electric current flows fed to the decoding device via the row lines and the column lines to determine at which of the sensor elements a sensor signal is present.

2. The sensor arrangement as claimed in claim 1, wherein the decoding device is divided into a row decoding device, to which accumulative electric current flows of the row lines are fed, and a column decoding device, to which accumulative electric current flows of the column lines are fed, the row decoding device determining, from at least a portion of the accumulative electric current flows of the row lines independently of the accumulative current flows of the column lines, information about those sensor elements at which a sensor signal is possibly present;

the column decoding device determining, from at least a portion of the accumulative electric current flows of the column lines independently of the accumulative current flows of the row lines, information about those sensor elements at which a sensor signal is possibly present; and the decoding device determining, from joint evaluation of the information determined by the row decoding device and the column decoding device, those sensor elements at which a sensor signal is present.

3. The sensor arrangement as claimed in claim 1, wherein the decoding device determines those sensor elements at which a sensor signal is present by:

Fourier transforming time-dependent accumulative current flows of the row lines and of the column lines;

multiplying together in pairs the Fourier-transformed accumulative current flows of the row lines and of the column lines; and inverse Fourier transforming the accumulative current flows multiplied together in pairs.

4. The sensor device as claimed in claim 1, wherein the decoding device determines whether a sensor signal is present at a sensor element by using at least one accumulative current flow of at least one adjacent row line and/or of at least one adjacent column line.

5. The sensor arrangement as claimed in claim 1, wherein the decoding device determines whether a sensor signal is present at a sensor element, by using at least one predetermined temporal and/or spatial reference signal.

6. The sensor arrangement as claimed in claim 5, wherein the at least one predetermined temporal and/or spatial reference signal is adapted to the determined sensor signal.

7. The sensor arrangement as claimed in claim 5, wherein at least two temporal and/or spatial reference signals are adapted to the determined sensor signal.

8. The sensor arrangement as claimed in claim 1, wherein the decoding device determines whether a sensor signal is present at a sensor element at a second instant, by using a predetermined item of reference information about sensor signals at a first instant, which first instant temporally precedes the second instant.

9. The sensor arrangement as claimed in claim 1, wherein the decoding device is configured as a maximum likelihood sequence estimation decoder or as a maximum a posteriori decoder.

10. The sensor arrangement as claimed in claim 1, further comprising a voltage source, which is coupled to at least a portion of the row lines and of the column lines such that a predetermined potential difference is provided for at least a portion of the coupling devices.

11. The sensor arrangement as claimed in claim 1, wherein the at least one coupling device is a current source controlled by the associated sensor element or a resistor controlled by the associated sensor element.

12. The sensor arrangement as claimed in claim 1, wherein the at least one coupling device has a detection transistor having a first source/drain terminal coupled to one of the row lines, a second source/drain terminal coupled to one of the column lines, and a gate terminal coupled to the sensor element assigned to the at least one coupling device.

13. The sensor arrangement as claimed in claim 1, wherein the at least one coupling device has a calibration device for calibrating the at least one coupling device.

14. The sensor arrangement as claimed in claim 13, wherein the calibration device has a calibration transistor having a first source/drain terminal coupled to the respective row line, a second source/drain terminal coupled to the gate terminal of the detection transistor and also to a capacitor coupled to the assigned sensor element, and a gate terminal coupled to a further column line, and an electrical calibration voltage is applied to the gate terminal of the calibration transistor by means of the further column line.

15. The sensor arrangement as claimed in claim 1, wherein the at least one coupling device has a deactivation function.

16. The sensor arrangement as claimed in claim 1, wherein the at least one coupling device has an amplifier element for amplifying individual electric current flow of the at least one coupling device.

17. The sensor arrangement as claimed in claim 16, wherein the amplifier element has a bipolar transistor having a collector terminal coupled to the respective row line, an emitter terminal coupled to the respective column line, and a base terminal coupled to the second source/drain terminal of the detection transistor.

18. The sensor arrangement as claimed in claim 1, wherein at least a portion of the row lines and of the column lines have an amplifier device for amplifying the accumulative electric current flow flowing in the respective row lines and column lines.

19. The sensor arrangement as claimed in claim 1, wherein at least a portion of the row lines and/or of the column lines have a sample/hold device for storing the accumulative electric current flow flowing in the respective row lines and/or column lines at a predeterminable instant.

20. The sensor arrangement as claimed in claim 1, wherein at least one sensor element is an ion-sensitive field-effect transistor (ISFET).

21. The sensor arrangement as claimed in claim 1, wherein at least one sensor element has a MOSFET.

22. The sensor arrangement as claimed in claim 1, wherein at least one sensor element is a sensor which is sensitive to electromagnetic radiation.

23. The sensor arrangement as claimed in claim 1, wherein the plurality of sensor arrays are formed essentially in rectangular fashion.

24. The sensor arrangement as claimed in claim 23, wherein the row lines form essentially a right angle with the column lines.

25. The sensor arrangement as claimed in claim 1, wherein the sensor arrays are formed essentially in honeycomb-shaped fashion.

26. The sensor arrangement as claimed in claim 25, wherein the row lines form an angle of 60° with the column lines, and wherein different column lines are either parallel to one another or form an angle of 60° with one another.

27. The sensor arrangement as claimed in claim 1, wherein the sensor arrangement is divided into at least two regions that can be operated independently of one another, and it is predetermined which of the at least two regions is operated.

* * * * *